United States Patent [19]

Rudolph et al.

[11] Patent Number: 5,242,792
[45] Date of Patent: Sep. 7, 1993

[54] METHOD FOR THE PRESERVATION OF RED BLOOD CELLS BY LYOPHILIZATION USING GLYCEROL OR INOSITOL WITH DISACCHARIDES

[75] Inventors: Alan S. Rudolph, Bowie, Md.; Joseph P. Larry, South Bend, Ind.

[73] Assignee: The United States of America as represented by the Secretary of the Navy, Washington, D.C.

[21] Appl. No.: 659,765

[22] Filed: Feb. 25, 1991

[51] Int. Cl.$^5$ .............................................. A01N 1/02
[52] U.S. Cl. ......................................... 435/2; 424/533
[58] Field of Search ...................... 435/2, 1; 424/533

[56] References Cited

U.S. PATENT DOCUMENTS

| | | | |
|---|---|---|---|
| 3,632,358 | 1/1972 | Echeandia et al. | 426/3 |
| 4,783,401 | 11/1988 | Horan et al. | 435/34 |
| 4,915,951 | 4/1990 | Baldeschwieler | 424/450 |
| 4,980,277 | 12/1990 | Junnila | 435/2 |
| 5,059,518 | 10/1991 | Kortright et al. | 435/6 |

FOREIGN PATENT DOCUMENTS 2254639  8/1975  France .

OTHER PUBLICATIONS

Crowe, J. H. et al., Cryobiology 27:219-231 (1990).
Arakawa, T. et al., Cryobiology 27:401-415 (1990).
Honadel, T. E. et al., Cryobiology 25:331-337 (1988).
Terada, T. et al., Jpn J Anim Reprod 35:20-25 (1989).
Kim et al, Korean J Anim Sci 31:768-773 (1989).
Wantanabe et al, J. Fac. Fish. Anim Husb. 11:33-37 (1972).
Singh, S. G. et al., In. Vet. Sci 37: 1-7 (1967).
Sherman, J. K., Fertil. Steril 14:49-64 (1963).
Rudolph et al., "A Calorimetric and Infrared Spectroscopic Study of the Stabilizing Solute Proline", Biophysical Society, vol. 50, Sep. 1986, pp. 423-430.
Bonderman et al., "A Lyophilized Hemoglobin Control Prepared from Stroma-Free Hemolysates", Clin. Chem., vol. 26, No. 2, 1980, pp. 305-308.
Heckley, "Effects of Oxygen on Dried Organisms", Academic Press, Inc., 1978, pp. 257-278.
Venuto et al., "Lyophilization of Crystalline Hemogloben Solution and Exchange Transfusions with Lyophilized, Reconstituted Hemoglobin", Surgery, Gynecology & Obsterics, Jan. 1979, vol. 148, pp. 69-75.
Thirion et al., "Circular Dichroism Studies of Freeze-Drying-Induced Conformation Changes in Human Hemoglobin", Biopolymers, vol. 22, 1983, pp. 2367-2381.

(List continued on next page.)

Primary Examiner—Douglas W. Robinson
Assistant Examiner—S. Saucier
Attorney, Agent, or Firm—Thomas E. McDonnell; Barry A. Edelberg

[57] ABSTRACT

The invention is directed to a composition comprising a permeabilizing agent, a preserving agent, and a buffered solvent. This composition is used to prepare the cells for lyophilization cells and to rehydrate the cells to recover them from lyophilization.

The process of this invention comprises adding the permeabilizing agent and the preserving agent in a buffered solution to red blood cells, agitating the combination for a period of time sufficient to allow permeation of the preserving agent into the cell, shell freezing the mixture, and lyophilizing the mixture. The dry lyophilized material can then be stored. The cells can be rehydrated using the same composition of permeability agent, preserving agent and buffered solvent.

10 Claims, 3 Drawing Sheets

OTHER PUBLICATIONS

Crowe et al., "Preservation of Freeze-Dried Liposomes by Trehalose", Archives of Biochem. and Biophys., vol. 242, No. 1, Oct. 1985, pp. 240-247.

Labrude et al., "Stability and Functional Properties of Haemoglobin Freeze-Dried in the Presence of Four Protective Substances After Prolonged Storage: Dose-Effect Relationships", J. Pharm. Pharmacol., 1983, vol. 35, pp. 23-27.

Harrigan et al., "Protection of Liposomes During Dehydration or Freezing", Chem. and Phys. of Lipids, vol. 52, 1990, pp. 139-149.

Beissinger et al., "Liposome-Encapsulated Hemoglobin as a Red Cell Surrogate", vol. 32, Trans. Am. Soc. Artif. Intern Organs., 1986, pp. 58-63.

Womersley et al., "Inhibition of Dehydration-Induced Fusion Between Liposomal Membranes by Carbohydrates as Measured by Fluorescence Energy Transfer", Academic Press, Inc., Cryobiology, vol. 23, 1986, pp. 245-255.

Crowe et al., "Factors Affecting the Stability of Dry Liposomes," Biochimia et Biophysica Acta 939, 1988, pp. 327-334.

Rudolph et al., "Membrane Stabilization During Freezing: The Role of Two Natural Cryoprotectants, Trehalose and Proline," Cryobiology, 22, 1985, pp. 367-377.

METHOD FOR THE PRESERVATION OF RED BLOOD CELLS BY LYOPHILIZATION USING GLYCEROL OR INOSITOL WITH DISACCHARIDES

BACKGROUND OF THE INVENTION

1. Field of the Invention

This invention relates to a method and composition for protecting mammalian cells, being preserved by lyophilization. More particularly, the invention pertains to a method and composition for introducing protective solutes into red blood cells to preserve the cell during lyophilization and for increasing the retention of useful cells on rehydration.

2. Description of the Prior Art

The preservation of labile proteins in the dry state by carbohydrates has been well documented (Bonderman, D. P., Proksch, G. J., and Haskins, S., "A Lyophilized Hemoglobin Control Prepared From Stroma-free Hemolysates," Clin. Chem., 26:2, 305-308, (1980); DeVenuto, F., Zegna, A. I., and Busse, K. R., "Lyophilization of Crystalline Hemoglobin Solution and Exchange Transfusions with Lyophilized, Reconstituted Hemoglobin," Surgery, Gynecology, and Obstetrics, 148, 69-75, (1979)). The recovery of functional hemoglobin (Hb) following lyophilization has been observed with a variety of carbohydrates (Thirion, C., Larcher, D., Chaillot, B., Labrude, P., and Vigneron, C., "Circular Dichroism Studies of Freeze-dried Induced Conformational Changes in Human Hemoglobin," Biopolymers, 22, 2367-2381, (1983)). The disaccharide trehalose has been shown in this work to be equally effective in retaining the functional oxygen binding characteristics of Hb as well as inhibiting oxidation of Hb to methemoglobin (metHb) in the dry state. The most likely mechanism of damage to proteins in the dry state is by free radical damage. Deleterious radicals accumulate in organisms that are damaged by severe dehydration, while those that accumulate protective carbohydrates maintain low levels of free radicals (Heckly, R. J., Effects of Oxygen on Dried Organisms in "Dry Biological Systems", (J. Crowe, ed.), 257-279, Academic Press, New York, 1978). One of the ways carbohydrates may protect biological systems from oxidative damage in the dry state is to act as scavengers of radicals that can oxidize essential biomacromolecules, Heckly supra. In these experiments, cold storage of lyophilized Hb (after rehydration) showed the rate of oxidative damage to Hb (as measured by the increase in metHb) is approximately the same as in those samples with added carbohydrates. This suggests that the protective antioxidant action of carbohydrates may be restricted to the dry state. This may be due to the half-life of the radical as it is thought to be much more stable in the absence of bulk water, Heckly supra. Another consideration is the use of these carbohydrates as substrates for bacterial growth in hydrated samples stored at 4° C. The presence of increasing amounts of bacterial endotoxins will also result in accelerated oxidation of Hb (unpublished data).

The ability of carbohydrates to maintain cell size during lyophilization is correlated to the ability of carbohydrates to inhibit dehydration. Previous work has demonstrated that trehalose, sucrose, and glucose (to a lesser degree) inhibit dehydration. This action may be due to the binding of carbohydrates to a cell wall or to a liposome (Crowe, L. M., Crowe, J. H., Rudolph, A. S., Womersley, C., and Appel, L., "Preservation of Freeze-dried Liposomes by Trehalose," Arch. Biochem. Biophys., 242:1, 240-247, (1985); Crowe, J. H., and Crowe, L. M., "Effects of Dehydration on Membranes and Membrane Stabilization at Low Water Activities," In Biological Membranes, (D. Chapman, Ed.), Vol. 5, Academic Press, New York/London, 1985; Rudolph, A. S., and Crowe, J. H., "A Calorimetric and Infrared Spectroscopic Study of the Stabilizing Solute Proline," Biophys. J., 50, 423-430 (1986)).

Baldeschwieler et al., in U.S. Pat. No.4,915,951, provides a summary of articles and patents relating to the discovery of and development of trehalose as a cryopreservation agent. Baldschwieler et al. discloses a lipophilic anchor molecule to assist in introducing a carbohydrate to the membrane wall. Disaccharides, such as maltose, are among the polyoxygen containing compounds which Baldeschwieler suggests as part of the cryopreservation agent.

Horan et al., in U.S. Pat. No. 4,783,401, discloses the use of osmolarity regulating agents to assist in introducing marking dyes into cells including blood cells. The suggested osmolarity regulating agents include sugars, sugar-alcohols, amino acids and certain hydrogen ion buffers known as "Good's Buffers". These osmolarity regulating agents include monosaccharides and disaccharides including glycerol, inositol and the like.

While freeze-thawing is now an accepted method of preserving a variety of mammalian cell lines, currently, there are no satisfactory methods of preserving red blood cells in the dry state. These red blood cells are inherently unstable to reduced water conditions because of oxidation events (expressed as generation of methemoglobin, the oxidative degeneration of hemoglobin) and destabilization of the cell membrane.

SUMMARY OF THE INVENTION

Accordingly, it is an object of this invention to improve the preservation of red blood cells by lyophilization;

Also, it is an object of this invention to suppress the formation of metHb in red blood cells when stored in the dry state for extended periods of time;

In addition, it is an object of this invention to have a method which increases the introduction of cryopreservation agents into mammalian cells including red blood cells;

Further, it is an object of this invention to provide a composition to prepare the cells for lyophilization and rehydrate the cells to increase the amount of useful cells available on rehydration.

These and additional objects of the invention are accomplished by a composition comprising a permeabilizing agent, a preserving agent, and a buffered solvent. This composition is used to prepare the cells for lyophilization cells and to rehydrate the cells to recover them from lyophilization.

The process of this invention comprises adding the permeabilizing agent and the preserving agent in a buffered solution to red blood cells, shaking the combination for a period of time sufficient to allow permeation of the preserving agent into the cell, shell freezing the mixture, and lyophilizing the mixture. The dry lyophilized material can then be stored. The cells can be rehydrated using the same composition of permeabilizing agent, preserving agent and buffered solvent.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

DESCRIPTION OF THE PREFERRED EMBODIMENTS

Figure 1:
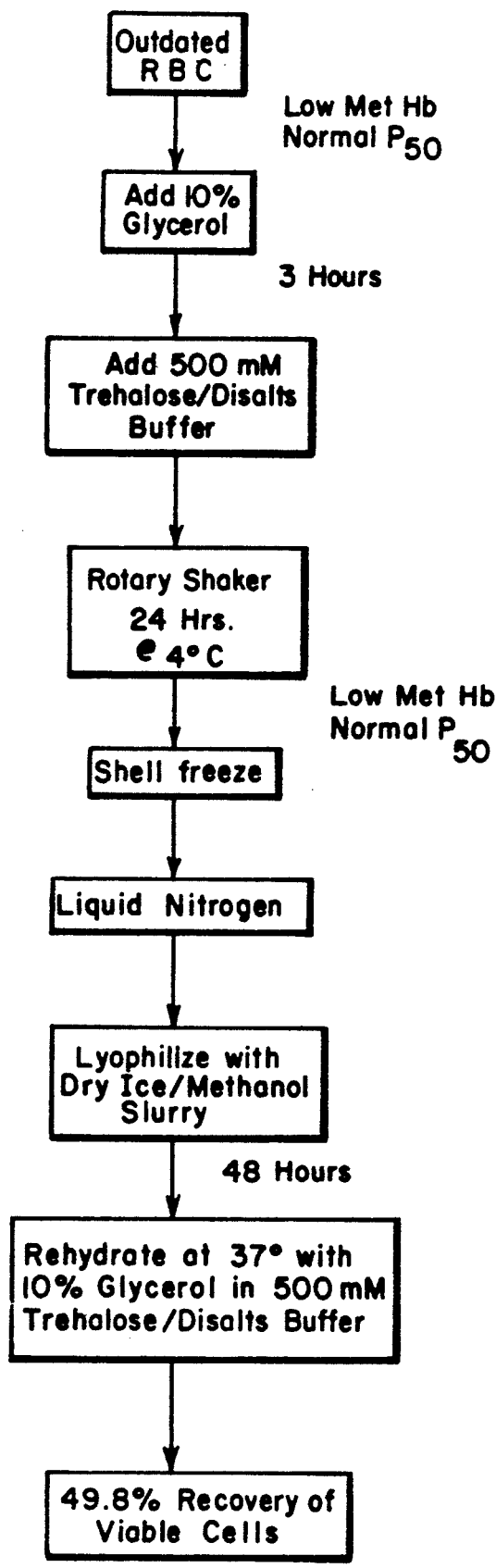
FIG. 1 is a flow chart of one embodiment of the process of this invention.

The invention is directed to the long term preservation of red blood cells for long term storage in a reduced mass (dry) form so the red blood cells can be available for transport to, storage in and use under non-hospital conditions. The composition of the invention involves the use of a protective agent such as sucrose, raffinose, proline, maltose, betaine, lactose, peptone and the unusual disaccharide, trehalose in combination with a permeabilizing agent such as a mono- or disaccharide sugar alcohols or mixtures thereof, for example glycerol or inositol or a mixture thereof, preferably glycerol in a buffered solution, to prepare the cell for lyophilization according to the method of the invention.

Trehalose, the preferred protective agent, is known to accumulate in organisms that survive complete dehydration. In the cell, trehalose acts by preserving biomembrane structure and function in the dry state by binding to hydration sites on the membrane. In addition, trehalose acts on soluble proteins in a similar manner and has shown antioxidant properties in the dry state. The introduction of trehalose into the interior of the cell and its interaction with the protein in the cell is important to preserving the cell and hemoglobin through lyophilization and storage.

The introduction of the preserving agent such as trehalose is improved by adding a membrane permeabilizing agent which increases the permeability of the red blood cell membrane to trehalose. The permeabilizing agent does not have to be chemical in nature but can be other means which will cause a cell membrane to become more permeable such as high electric fields to introduce pores in the cell membrane. This technique (electroporation) has been successfully used to transfect bacterial cells and introduce other genetic materials into mammalian cells.

The introduction of trehalose to the cell interior results in enhanced preservation of the cell membrane and interaction with the soluble protein, hemoglobin, responsible for oxygen transport. The interaction of trehalose with hemoglobin is important because oxidation of the protein induced by drying is prevented. Preferably, the preserving agent and the permeabilizing agent are in a buffered solution which will also include the red blood cells.

The preserving agent should be in a concentration of between 100 and 500 mM, preferably a concentration of between 300 and 500 and most preferably about 400 to about 500. The permeabilizing agent should be in a concentration of between 1 and 10 weight percent, preferably between 5 and 10 weight percent and most preferably between 7 and 10 weight percent. The buffer is preferably isotonic. Alternative buffers which can be used are other buffers currently used to suspend red blood cells such as lactated Ringer's, hypertonic saline, and citrate dextrose.

The method of preparing mammalian cells for dry storage comprises: mixing the mammalian cells with a preserving composition comprising a permeabilizing agent and a protective agent in a buffered solution; agitating the cells for a time sufficient for the protective agent to interact with the membrane of the cell and with the proteins present in the cell; freezing and subsequently lyophilizing the combination of red blood cells preserving composition; and recovering and storing the dry, lyophilized product. In the preferred method, the process involves preparing red blood cells for dry storage comprising adding a cell membrane permeabilizing agent to suspension of red blood cells; adding a buffered solution containing a protective agent in the form of a sugar selected from the group consisting essentially of sucrose, raffinose, proline, maltose, betaine, lactose peptone and trehalose to form a preservative composition; agitating the preservation composition for a time sufficient for the protective agent to interact with the cell membrane and to enter into the cell and interact with the available proteins including hemoglobin; freezing and lyophilizing the preservation composition; and recovering the dry product.

Having described the invention, the following examples are given to illustrate specific applications of the invention including the best mode now known to perform the invention. These specific examples are not intended to limit the scope of the invention described in this application.

EXAMPLE 1

The described method involves the incubation of a cell suspension with a mixture of glycerol as the permeabilizing agent and trehalose as the protective disaccharide. FIG. 1 is a flow chart outlining the process. In a lyophilization jar of 300 ml volume, a suspension of red blood cells is placed that has been diluted with a solution containing 10% glycerol by weight and 500 mM trehalose in a buffered solution of a standard isotonic phosphate buffered saline at pH =7.4. This suspension is allowed to agitate for at least 12 hours (at 4.C) at which time the suspension is shell frozen in liquid nitrogen and placed on the lyophilizer packed in dry ice. The rehydration of this material is accomplished by rehydration with the same solution of glycerol, trehalose and buffer at 37.C or alternatively, in a high humidity chamber. The purpose of the latter rehydration scheme is to effect a more gentle rehydration to enhance recovery of intact cells.

EXAMPLE 2

The advantage of the described invention is that it allows the recovery of intact cells that function normally following lyophilization. The combination of a permeabilizing agent and the protective sugar is a superior method for incorporating the sugar into the intracellular compartment. Another advantage of the described invention is that the protective regime does not require the protectants to be washed out before transfusion because the added carbohydrate is a source of metabolic fuel needed in the system. This is illustrated by analysis of the material formed in Example 1. The rehydrated material is assayed for percentage of intact cells, the induction of methemoglobin, and the oxygen carrying capacity. The results of rehydration of freeze-dried red cells that have been treated with the described invention and unprotected controls are presented in FIGS. 2 through 4 expressing methemoglobin recovery, oxygen carrying capacity and % cell recovery.

Figure 2:
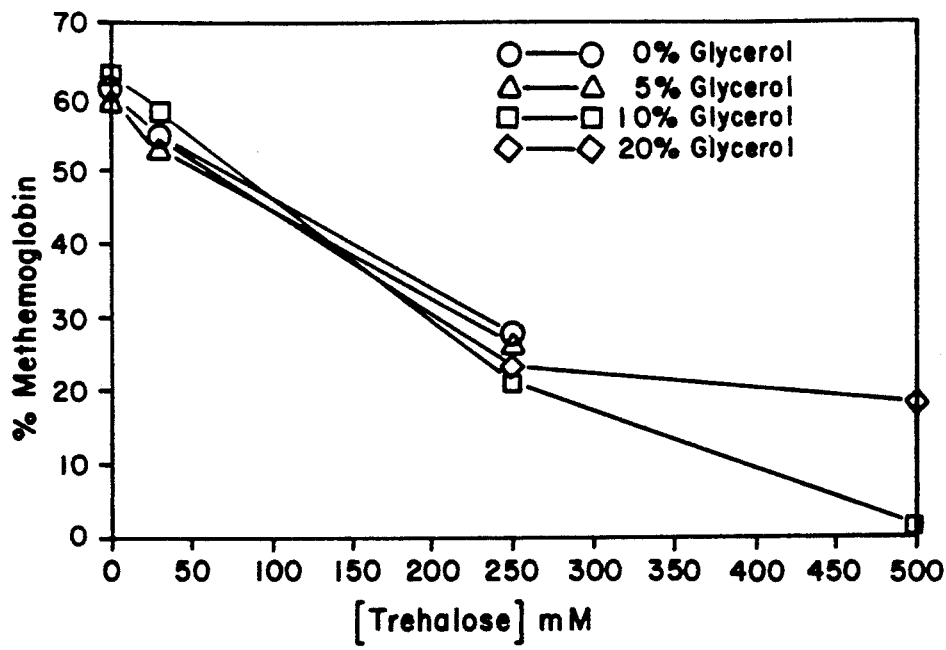
FIG. 2 is a graph of an embodiment of the invention depicting variations of MetHb plotting the percentage Methemoglobin against concentration of trehalose.

As shown in FIG. 2, the amount of methemoglobin markedly decreases as the trehalose concentration that the cells are exposed to after glycerol exposure is increased. The methemoglobin levels are measured using a colorimetric assay described in S. Tomita et al., "A simple spectrophotometric method for the determination of methemoglobin in dilute solutions", *J. Nara. Med. Assoc.*, 19, 1 (1968), incorporated herein by reference. In the absence of any protection, 60% of the hemoglobin is converted to the methemoglobin form. At 250 mM trehalose, increasing the glycerol concentration during the initial permeabilization step results in a decreased level of methemoglobin (20% for 10% glycerol and 250 mM trehalose). The optimum recovery of oxyhemoglobin is observed with 10% glycerol and 500 mM trehalose where there is no measurable methemoglobin. The inhibition of methemoglobin formation is essential as this form of hemoglobin cannot carry oxygen.

Figure 3:
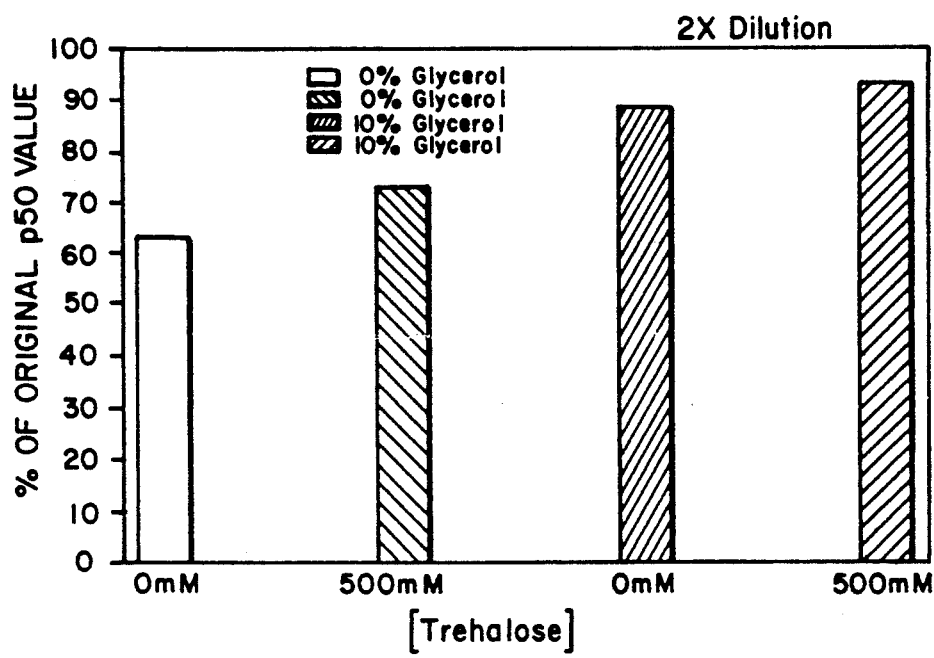
FIG. 3 is a graph of an embodiment of this invention depicting change in $P^{50}$ values from fresh blood plotting percent of original $P^{50}$ value against concentration of trehalose.

The oxygen carrying capacity is a measure of the cooperativity of oxygen binding and relates to the structural integrity of tetrameric oxyhemoglobin. The oxygen carrying capacity is expressed as a $P_{50}$ value. This value for normal human blood is 26 (for a male). The values for the freeze-dried blood are expressed, in FIG. 3, as a percentage of this original value (taken before the freeze-drying protocol). As shown in FIG. 3, no protection results in a loss of 60% of the original $P_{50}$ value, while the addition of 500 mM trehalose (no glycerol) increases this value approximately 10% As also shown in FIG. 3, the initial permeabilization step, in the absence of any subsequent addition of trehalose, results in a 90% recovery of the $P_{50}$ value, while the highest recovery of the value is accomplished with 10% glycerol and 500 mM trehalose using the optimum procedure described previously.

Figure 4:
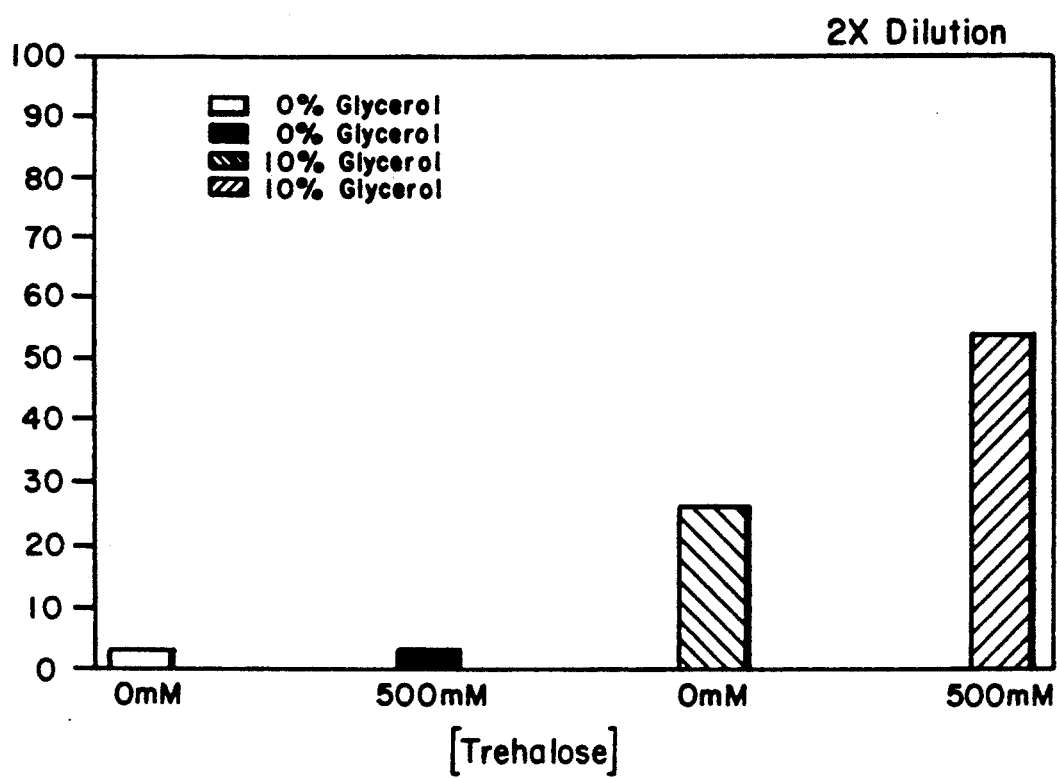
FIG. 4 is a graph of an embodiment of this invention depicting percent cell recovery after lyophilization (2×dilution) plotting percent glycerol against concentration of trehalose.

Perhaps the most important measure of success is the recovery of intact cells using the procedure described, shown in FIG. 4. The number of intact cells recovered with no protection, 500 mM trehalose, 10% glycerol without trehalose, and 10% glycerol with 500 mM trehalose, reveals that the highest recovery occurs with 10% glycerol and 500 mM trehalose.

Obviously, many modifications and variations of the present invention are possible in light of the above teachings. It is therefore to be understood that, within the scope of the appended claims, the invention may be practiced otherwise than as specifically described.

What is claimed is:

1. A method of preparing mammalian red blood cells for dry storage comprising the steps of:
   mixing the red blood cells with a preserving composition comprising a protective agent in a buffered solution, said protective agent being selected from the group consisting of sucrose, raffinose, maltose, lactose and trehalose;
   permeabilizing said red blood cells in said preserving composition by subjecting them to a permeabilizing agent selected from the group consisting of inositol and glycerol;
   agitating the cells for a time sufficient for the protective agent to interact with the membrane of the cell and with the proteins present in the cell;
   freezing and subsequently lyophilizing the combination of red blood cells and preserving composition; and
   recovering and storing the dry, lyophilized product.

2. A method according to claim 1 wherein the buffer is selected from the group consisting of lactated Ringer's, hypertonic saline, and citrate dextrose.

3. A method according to claim 1 wherein said red blood cells are permeabilized by subjecting them to said permeabilizing agent present in a concentration of between approximately 1 and 10% by weight and wherein the protective agent is present in a concentration of between approximately 100 and 500 mM before lyophilization.

4. A method according to claim 4 wherein the permeabilizing agent is present in a concentration of between approximately 5 and 10% by weight and the protective agent is present in a concentration of between approximately 300 and 500 mM before lyophilization.

5. A method according to claim 4 wherein the permeabilizing agent si glycerol and the protective agent is trehalose.

6. The method of claim 1, wherein said lyophilized product is rehydrated and transfused into a mammal.

7. The method of claim 6, wherein said red blood cells are human red blood cells and wherein said rehydrated product is transfused into a human.

8. The method of claim 1, wherein said protective agent is trehalose.

9. The method of claim 1, wherein said permeabilizing agent is glycerol.

10. The method of claim 9, wherein said protective agent is trehalose.

* * * * *